United States Patent [19]
Christensen

[11] Patent Number: 4,479,947
[45] Date of Patent: Oct. 30, 1984

[54] ORAL ABSORPTION ENHANCEMENT OF CARBOXYLIC ACID PHARMACEUTICALS USING (5-ALKYL-2-OXO-1,3-DIOXOLEN-4-YL)METHYL ESTER GROUP

[75] Inventor: Burton G. Christensen, Cliffside Park, N.J.

[73] Assignee: Merck & Co., Inc., Rahway, N.J.

[21] Appl. No.: 385,199

[22] Filed: Jun. 7, 1982

Related U.S. Application Data

[63] Continuation-in-part of Ser. No. 366,036, Apr. 6, 1982, abandoned, which is a continuation-in-part of Ser. No. 344,413, Feb. 1, 1982, abandoned, which is a continuation-in-part of Ser. No. 324,728, Nov. 25, 1981, abandoned, which is a continuation-in-part of Ser. No. 285,170, Jul. 18, 1981, abandoned, which is a continuation-in-part of Ser. No. 282,821, Jul. 13, 1981, abandoned.

[51] Int. Cl.³ ............... A61K 31/545; A61K 31/665; C07D 499/00; C07D 501/46; C07D 317/24; C07D 277/40
[52] U.S. Cl. .................. 424/203; 260/239.1; 260/245.2 R; 260/245.2 T; 260/245.4; 424/232; 424/246; 424/290; 424/291; 424/278; 544/21; 544/29; 546/189; 548/194; 548/196; 548/344; 548/494; 548/500; 548/531; 548/532; 548/533; 548/535; 549/229

[58] Field of Search ............ 260/239.1, 245.2 R, 260/245.2 T, 245.4; 544/21, 29; 548/196, 194, 344, 494, 500, 531, 532, 533, 535; 424/246, 271, 270, 278, 232, 203; 549/229; 546/189

[56] References Cited

U.S. PATENT DOCUMENTS

| | | | |
|---|---|---|---|
| 3,873,521 | 3/1975 | Ekstrom et al. | 260/239.1 |
| 3,939,270 | 2/1976 | Ekstrom et al. | 424/271 |
| 4,109,084 | 8/1978 | Gordon | 544/29 |
| 4,342,693 | 8/1982 | Sakamoto et al. | 549/229 |

Primary Examiner—Natalie Trousof
Assistant Examiner—Vera C. Clarke
Attorney, Agent, or Firm—Thomas E. Arther; Hesna J. Pfeiffer

[57] ABSTRACT

The (5-R-2-oxo-1,3-dioxolen-4-yl)methyl moiety:

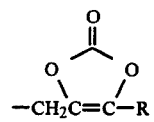

wherein R is loweralkyl of 1-6 carbon atoms, especially methyl or t-butyl; when utilized as an ester on a pharmaceutical having a carboxylic acid functionality, enhances oral absorption of the pharmaceutical. This effect is applicable to a broad range of pharmaceutically active substances, including antibiotics, and antihypertensives as well as other classes of therapeutic agents.

11 Claims, No Drawings

ORAL ABSORPTION ENHANCEMENT OF CARBOXYLIC ACID PHARMACEUTICALS USING (5-ALKYL-2-OXO-1,3-DIOXOLEN-4-YL)METHYL ESTER GROUP

RELATIONSHIP TO OTHER APPLICATIONS

This application is a continuation-in-part of U.S. Ser. No. 366,036, filed Apr. 6, 1982, now abandoned which in turn is a continuation-in-part of U.S. Ser. No. 344,413, filed Feb. 1, 1982, now abandoned, which in turn is a continuation-in-part of U.S. Ser. No. 324,728, filed Nov. 25, 1981, now abandoned, which in turn is a continuation-in-part of U.S. Ser. No. 285,170, filed July 18, 1981, now abandoned; which in turn is a continuation-in-part of U.S. Ser. No. 282,821, filed July 13, 1981, now abandoned;

SUMMARY OF THE INVENTION

This invention provides a novel moiety

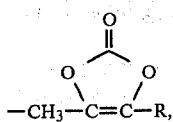

I wherein R is loweralkyl of 1–6 carbon atoms, especially methyl or t-butyl; which when present as an ester of a carboxylic acid, enhances oral absorbability of the ester product.

The useful esters of this invention are prepared by utilizing the alcohol or halide, e.g. chloride or bromide form of group I above in reaction with the free acid or salt form of the desired pharmaceutically active compound of which enhanced oral absorption is desired. Preferably, the bromide form:

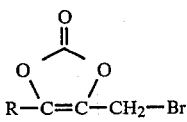

II (the 5-methyl compound is prepared as described by H. Scherf and H. Plum, Liebiegs Ann. Chem., 1977, 27–32, and the other 5-alkyls, including 5-t-butyl, are prepared in a similar fashion) is reacted with either the lithium or silver salt form of the pharmaceutical acid.

Preferable reaction conditions include a ratio of from about equivalent to twice equivalent amounts of Compound II to the pharmaceutical acid, in a solvent such as hexamethylphosphoramide, dimethylformamide, acetronitrile, dimethyl sulfoxide, or the like, at from about 0°–50° C., preferably about 25°–35° C., for from 2–24 hours, (the reaction proceeds more quickly at the higher end of the range).

The ester can be recovered in from 10–60% yield, and is purified by recrystallization in an appropriate solvent system, such as ethylacetate-diethyl ether.

The preparation of the (5-methyl-2-oxo-1,3-dioxolen-4-yl)methyl ester of cefoxitin illustrates one embodiment of this invention.

EXAMPLE 1

Step A. Preparation of Cefoxitin Lithium Salt

To a stirred suspension of 42.75 g (0.1 m) of cefoxitin in 1 liter of water is added at 0°–5° over a period of 45–60 minutes a solution of 0.1N lithium hydroxide. The initial pH of the mixture is about 3.0. Addition of the alkaline solution is so regulated that the pH does not rise above 5.5. The solution, about 2.5 liters, is filtered to remove a small amount of undissolved free acid and then subdivided in equal portions into 5×5 liter round bottom flasks for lyophilization and for use in the next steps.

Step B. Esterification

Fifty-four grams (0.125 m) of cefoxitin Li salt is charged into a 3-liter, 3-necked round bottom flask, fitted with a stirrer and Drierite tube. The solid is stirred and 540 ml of hexamethylphosphoramide (HMPA), pH 6.7, is added. Upon the addition of (5-methyl-2-oxo-1,3-dioxolen-4-yl)methyl bromide, (0.25 m), the temperature rises slightly, and is kept at about room temperature, while stirring 20 minutes. Esterification is monitored by tlc (silica gel plates, ethylacetate-chloroform solvent).

After the end of the reaction period, the solution is added to a stirred mixture of 5 liters of water and 5 liters of ethyl acetate. The separated aqueous phase is extracted with 2×2 liters of ethyl acetate, and the combined solution is washed with 2×2 liters of water and 1×2 liters of saturated sodium chloride solution. The solution is dried over anhydrous magnesium sulfate, treated with 15 g of Darco G-60, and after filtration, concentrated under vacuum at room temperature. The concentrate is dissolved in 270 ml of methylene chloride, and the resulting solution added slowly to 13 liters of petroleum-benzin with rapid stirring. The precipitate is filtered off, washed with petroleum-benzin and dried at r.t./0.1 mm/18 hrs./$P_2O_5$.

Step C. Purification

The above impure ester is dissolved in 400 ml of ethyl acetate at room temperature. The solution is treated with 2×7.0 g of Darco G-60, washing the charcoal cake well after each treatment with ethyl acetate. The combined filtrate and washes are concentrated at room temperature at 2–5 mm to a volume of about 500 ml. To the stirred concentrated solution under anhydrous conditions is added slowly 700 ml of ethyl ether to the point of producing a first permanent cloudiness. The solution is clarified with a few drops of ethyl acetate and then ether (ca 5 ml) is carefully added to cloudiness again. After stirring for a few minutes, the solution is allowed to stand undisturbed at room temperature for 3–4 hours, and then aged at 5° overnight. The mixture is filtered, and the solid washed with 3×50 ml of ether. The cefoxitin ester is dried at r.t./0.1 mm/$P_2O_5$/24 hours.

Alternatively, the silver salt of cefoxitin can be prepared by reacting 1 equivalent of cefoxitin free acid with 1 equivalent sodium bicarbonate in water then adding the resulting solution to a solution of 2 equivalents of silver nitrate in aqueous solution. The silver salt precipitates, is dried and used as the starting material in reaction with the (5-methyl-2-oxo-1,3-dioxolen-4-yl)methyl bromide, as described above, as a suspension in anhydrous acetonitrile.

The final product, (5-methyl-2-oxo-1,3-dioxolen-4-yl)methyl ester of cefoxitin can be administered to humans at the usual dosage levels and regimen as cefoxitin sodium, a widely available product. The product can be given IV or orally, at levels of 2–20 mg/kg/day. Blood levels of drug are enhanced in comparison with cefoxitin sodium.

Other Pharmaceutical Products

Many other antibiotics and antibacterials can have enhanced blood levels, if they are employed in the form of the (5-alkyl-2-oxo-1,3-dioxolen-4-yl)-methyl ester. The ester form of these compounds is prepared using the same general procedure described above for the cefoxitin ester. In addition, any therapeutic pharmaceutical, if it possesses a carboxylic acid group can be used in the (5-methyl-2-oxo-1,3-dioxolen-4-yl)methyl ester form, to yield enhanced absorption and higher blood levels. All of these ester-containing pharmaceuticals are used at dosage levels and regimen as the parent acid or salt form, and are prepared as decribed above.

Included within the meaning of the terms "pharmaceutical acid" or "therapeutic pharmaceutical" are the following compounds:

1. ethacrynic acid, [2,3-dichloro-4-(2-methylene butyryl)phenoxy]acetic acid;
2. mercaptobutanedioic acid;
3. metyrosine, (−) α-methyl-L-tyrosine;
4. penicillamine;
5. phthalylsulfathiazole, 4'-(2-thiazolylsulfamoyl)phthalanilic acid;
6. probenecid, 4-[(dipropylamino)sulfonyl]benzoic acid;
7. flufenisal, 4-(acetyloxy)-4'fluoro-[1,1'-biphenyl]-3-carboxylic acid;
8. methyldopa, levo-3-(3,4-dihydroxyphenyl)-2-methylalanine;
9. carbidopa, (−)-L-α-hydrazino-α-methyl-β-(3,4-dihydroxybenzene)propanoic acid monohydrate;
10. levodopa, (−)-L-α-amino-β-(3,4-dihydroxybenzene)propanoic acid;
11. (S)-3,4-dihydroxy-α-methyl phenylalanine;
12. sulindac, Z-5-fluoro-2-methyl-1-[[p-methylsulfinyl)phenyl]methylene]-1H-indene-3-acetic acid;
13. 5-(1-pyrrolyl)salicylic acid;
14. 12-hydroxy-8-methylsulfonylheptadecanoic acid;
15. Z-2-(((2,2-dimethylcyclopropyl)carbonyl)amino)-α-octenoic acid;
16. (R)-8-fluorodibenzo(b,f)thiepin-3-carboxylic acid-5-oxide;
17. (+)-4-3-3-[2-(1-hydroxycyclohexyl)ethyl]-4-oxo-2-thiazolidinyl propyl benzoic acid;
18. (+)-α-(fluoromethyl)histidine hydrochloride;
19. (6,7-dichloro-2-cyclopentyl-2-methyl-1-oxo-5-indanyloxy)acetic acid;
20. 3-fluoro-D-alanine-2-deuterium labeled.
21. 10,11-dihydro-5-(1-methyl-4-piperidinylidine)-5H-dibenzo(a,d)cycloheptene-3-carboxylic acid hydrochloride;
22. N-formimidoyl thienamycin monohydrate;
23. (Z)-7(R)-[(2-amino-2-carboxyethylthio)-2-(S)-[(2,2-dimethylcyclopropyl)carbonyl]amino-2-heptenoic acid;
24. 3β-[2-methoxyamino-2-(2-amino-1,3-thiazol-4-yl)acetamido]monobactamic acid;
25. N-[(S)-1-(carboxyl)-3-phenylpropyl]-L-alanyl-L-proline maleate;
26. N²-[1-(S)-carboxy-3-phenylpropyl]-L-lysyl-L-proline;
27. N-[1(S)-carboxy-3-phenylpropyl]-L-alanine-L-proline;
28. dihydroxyphosphine carboxylic acid oxide;
29. moxalactam, 7β-(α-hydroxyphenyl)-L-carboxyacetamido)-7α-methoxy-3-(1-methyltetrazo-5-yl)thiomethyl-1-oxadethia-3-cephem-4-carboxylic acid;
30. somatostatin;
31. thienamycin;
32. cefmetazole, (6R,7S)-7-[2-(cyanomethylthio)acetamido]-7-methoxy-3-[(1-methyl-1H-tetrazol-5-yl)thiomethyl]-8-oxo-5-thia-1-azabicyclo[4.2.0]oct-2-ene-2-carboxylic acid;
33. cefmenoxime, 7-[α-(2-aminothiazol-4-yl)-α-methoxyiminoacetamido]-3-(1-methyl-1H-tetrazol-5-ylthiomethyl)-3-cephem-4-carboxylic acid;
34. 7β-[D-(−)-α-(4(5)-carboxyimidazole-5(4)-carboxamidophenylacetamido]-3-(4-β-sulfoethylpyridinium)methyl-3-cephem-4-carboxylic acid;
35. 7-[D-α-[3-(2'-aminosulfonylanilino-4-hydroxy-5-pyrimidinyl)ureido]-p-hydroxyphenyl-acetamido]-3-[1-methyltetrazo-5-yl)thiomethyl]-ceph-3-em carboxylic acid;
36. ceforanide, 7-(2-aminomethylphenylacetamido)-3-1-carboxymethyl tetrazol-5-ylthiomethyl)-3-cephem-4-carboxylic acid;
37. ceftizoxime, 7-[2-methoxyimino-2-(2-amino-1,3-thiazol-4-yl)acetamido]cephalosporanic acid;
38. ceftazidime, (1-[7-[2-(2-amino-4-thiazolyl)glyoxylamido]-ceph-3-em-3-yl-methyl]pyridinium hydroxide, inner salt;
39. cefotetan, (6R,7S)-7-[4-(carbamoylcarboxymethylene)-1,3-diethietane-2-carboxamido]-7-methoxy-3-[[(1-methyl-1H-tetrazol-5-yl)thio]methyl-8-oxo-5-thia-1-azabicyclo[4.2.0]oct-2-ene-2-carboxylic acid;
40. cefsulodin, 7-(α-Sulphophenylacetamido)-3(4'-carbamoylpyridinium)methyl-3-cephem-4-carboxylate;
41. 7-[D(−)-α-(4-hydroxy-6-methylpyridine-3-carboxamido)-α-(4-hydroxyphenyl)-acetamido]-3-[(1-methyl-1H-tetrazol-5-yl)thiomethyl]-3-cephem-4-carbxylic acid;
42. cefatriaxon, (6R,7R)-7-[2-(2-amino-4-thiazolyl)glyoxylamido]-3-[[(2,5-dihydro-6-hydroxy-2-methyl-5-oxo-as-triazin-3-yl)thio]methyl-8-oxo-5-thia-1-azabicyclo[4.2.0]oct-2-ene-2-carboxylic acid 7(Z)²-(O-methyloxime);
43. cefaperazone, 7-[D-(−)-α(4-ethyl-2,3-dioxo-1-piperazinecarboxamido)-α-(4-hydroxyphenyl)acetamido]-3-[(1-methyl-1H-tetrazol-5-yl)thiomethyl]-3-cephem-4-carboxylic acid;
44. 7β-(D-2-amino-2-carboxy-ethylthio)acetamido-7α-methoxy-3-[(1-methyl-1H-tetrazol-5-yl)thiomethyl] ceph-3-em-4-carboxylic acid;
45. cefotaxime,3-acetoxymethyl-7-[2-(2-amino-4-thiazolyl-2-methoxy-imino]acetamido-3-cephem-4-carboxylic acid;
46. penicillin;
47. 2-(ethylthio)-6β-(1R-hydroxyethyl)-penem-3-carboxylic acid;
48. cephalexin;
49. furosemide;
50. ibuprofen;
51. cephalexin;
52. aspirin;
53. sodium levothyroxine;
54. amoxicillin;
55. penicillin V;
56. naproxen;
57. fenoprofen;
58. 7-theophyllineacetic acid;
59. tolmetin;
60. clofibric acid;
61. cefaclor;
62. ceforanide;
63. pirprofen;

64. isoxepac;
65. benoxaprofen;
66. suprofen;
67. cefotaxime;
68. diclofenac sodium;
69. corprofen;
70. flurbiprofen;
71. naprosyn;
72. fosfomycin.

Other compounds can be used. All of the above compounds are known in the art in the acid or sodium salt form. Their dosage form, dosage regimen and indications as the (5-methyl-2-oxo-1,3-dioxolen-4-yl)methyl ester is the same as the free acid or pharmaceutically accepted salt or ester forms already published. The advantage of the ester group yields enhanced blood levels of the active compound in the human or animal being treated.

Another group of compounds which can be employed to form the ester are those disclosed in U.S. Pat. No. 4,146,719, a group of quinoline carboxylic acids. One particularly preferred compound in this patent is 1-ethyl-6-fluoro-1,4-dihydro-4-oxo-7-(1-piperazinyl)-3-quinoline carboxylic acid. The ester forms are employed in the same dosage form and regimen as in U.S. Pat. No. 4,146,719, which is incorporated by reference. An example teaching how to make the 5-methyl-1,3-dioxol-4-en-2-on-4-yl methyl ester of the compound 1-ethyl-6-fluoro-1,4-dihydro-4-oxo-7-(1-piperazinyl)-3-quinoline carboxylic acid follows. It is noted that the nitrogen on the quinoline ring is first blocked using a trimethyl silyl blocking group, although any similar blocking group can be employed. This blocking group is then displaced with 2-trimethylsilylethoxycarbonyl chloride, the ester group formed, and the blocking group removed by trifluoroacetic acid. Other similar blocking and unblocking steps can be employed to yield the desired ester. A similar procedure is used to prepare the 5-t-butyl-1,3-dioxol-4-en-2-on-4-yl methyl ester of the compound 1-ethyl-6-fluoro-1,4-dihydro-4-oxo-7-(1-piperazinyl)-3-quinoline carboxylic acid.

EXAMPLE 2

Step A. Preparation of 1-Ethyl-6-fluoro-1,4-dihydro-4-oxo-7-[4(2-trimethylsilylethoxycarbonyl)piperazin-1-yl]-3-quinoline carboxylic Acid (3).

To a suspension of 1-ethyl-6-fluoro-1,4-dihydro-4-oxo-7(piperazin-1-yl)-3-quinoline carboxylic acid, 1.0 g, (3.13 mmole), in 10 ml of sieve dried methylene chloride, is added triethylamine, 950, (690 mg; 6.83 mmole). The mixture is heated with stirring in a $N_2$ atmosphere until refluxing begins, the heating bath is removed, and trimethylsilyl chloride, 900, (770 mg; 7.07 mmole) is added in rapid dropwise fashion, with continued stirring. The suspension clears towards the end of the addition, then clouds again slightly as the last of the chloride is added. The mixture is stirred and heating to reflux resumed for 1 hour. The resultant solution of 2 is cooled in an ice-bath, and triethylamine, 475, (345 mg; 3.41 mmole), is added, followed by 2-trimethylsilylethoxycarbonyl chloride, 600, (564 mg; 3.13 mmole; *J.C.S. Chem. Comm.*, 358 (1978)) with continued stirring. After ice-bath removal, the mix is allowed to stir for 1.5 hours, after which solvent is removed by evaporation under a $N_2$ stream. The resultant purplish solid is slurried with 10 ml of a 5% aqueous citric acid solution, centrifuged, and the precipitate of 3 washed twice with water. The resultant paste is spread over the inside of the centrifuge tube and dried with a gentle $N_2$ stream. In 9:1/CHCl$_3$:MeOH, the tlc shows an elongated, but relatively homogeneous spot which is significantly more mobile than 1. Chromatography on 30 g Baker silica gel with 2% MeOH/CH$_2$Cl$_2$ gives after an initial 100 ml void volume a series of 8-10 ml fractions; the bulk of the product appears in fractions 7-14, with traces in 6 and 15-30. Combining 7-14, 559 mg of product is obtained. The pmr (200 MHz) showed the following peaks: (CDCl$_3$) 0.01 (Si(CH$_3$)Si), 0.98 and 1.02 (each CH$_2$N of piperazine), 4.38-4.14 (m; CH$_2$O and CH$_2$CH$_3$), 6.83 (d, $J_{6,8}=7$ Hz; H$_8$), 8.07 (d, $J_{5,6}=13$ Hz; H$_5$), 9.78 (S; H$_2$) ppm.

Step B Preparation of 5-Methyl-1,3-dioxol-4-en-2-on-4-ylmethyl 1-Ethyl-6-fluoro-1,4-dihydro-4-oxo-7[4(2-trichloroethoxycarbonyl)piperazin-1-yl]-3-quinoline carboxylate (5).

To a solution of 55 mg LiOH·H$_2$O (1.31 mmole) in 20 ml water is added 559 mg of 3 (1.21 mmole) with swirling; dissolution is greatly aided by brief sonication, to give a somewhat opalescent solution of 4 which is then lyophylized. The resultant white residue is treated with 5 ml of dry hexamethylphosphoramide containing 583 mg of 4-bromomethyl-5-methyl-1,3-dioxol-4-en-2-one as an 50% mix with unbrominated material (1.9 mmole) (*Ann.* 27 (1977)). Solution is aided if a small magnetic stirring bar is present to help in wiping the walls with the limited volume of liquid. After stirring for 3 hours, the solution is diluted with 50 ml petroleum ether and stirred for another half hour. The oil which separates is washed once with petroleum ether and purified by chromatography on silica gel using 1% methanol in methylene chloride. After recrystallization, an analytical sample, m.p. 145° (d), gives the following:

Calcd. for C$_{27}$H$_{34}$FN$_3$O$_8$Si: C, 56.33; H, 5.95; N, 7.30. Found: C, 56.11; H, 5.95; N, 7.19.

The pmr (200 mHZ) spectrum had peaks at (CDCl$_3$) 0.0 (S; CH$_3$Si) 1.01 and 0.96 (each d, J=8 Hz; CH$_2$Si), 1.51 (t, J=6; CH$_3$CH$_2$), 2.20 (S; CH$_3$C(O)=C) 3.11-3.23 and 3.71-3.59 (m; NCH$_2$'S of piperazine), 4.26-4.11 (m; OCH$_2$CH$_2$ and CH$_2$CH$_3$), 5.03 (S; OCH$_2$-C(O)=C), 6.73 (d, $J_{6,8}=7$; H$_8$), 8.06 (d, $J_{5,6}=13$; H$_5$), 8.40 (S; H$_2$) ppm.

Step C. Preparation of 5-Methyl-1,3-dioxol-4-en-2-on-4-yl-methyl-1-Ethyl-6-fluoro-1,4-dihydro-4-oxo-7-(piperazin-1-yl)-3-quinoline Carboxylic Acid (6).

A solution of 40 mg of 5 in 0.5 ml of trifluoroacetic acid is held at 0° for ten minutes, then evaporated to a gum under aspirator pressure and held there at ambient temperature for 2-3 minutes. The residue is triturated with 5 ml water, adding small portions of sodium bicarbonate to bring the pH to near 7. The suspension is stirred for 15 minutes, the solid collected by centrifugation, then washed several times with small volumes of water. After spreading the paste on the walls of the centrifuge tube, a gentle stream of nitrogen is blown over it until dry. The resultant 6 gave a pmr (200 mHz) with peaks at (DMSO-d$_6$) 1.38 (t, J=7 Hz; CH$_3$CH$_2$), 2.23 (S; CH$_3$C(O)=C), 3.26-3.39 and 3.42-3.52 (b; NCH$_2$'S of piperazine), 4.57-4.41 (bQ, J=7 Hz; CH$_2$CH$_3$), 5.13 (s; OCH$_2$C(O)=C), 7.15 (d, $J_{6,8}=8$ Hz; H$_8$), 7.88 (d, $J_{5,6}=13$ Hz; H$_5$), 8.72 (S; H$_2$) ppm.

EXAMPLE 3

Preparation of (4-methyl-1,3-dioxol-2-one-5-yl-methyl)ester of methyldopa

Step A. (S)N-(t-Butylcarbonyl)-3-hydroxy-α-methyltyrosine

A mixture of (S) 3-hydroxy-α-methyltyrosine sesquihydrate [methyldopa] (5.0 g, 21 mmol), triethylamine (2.1 g, 21 mmol) and di t-butyl dicarbonate (4.9 g, 23 mmol) in dimethylformamide, 50 mL, is stirred at 20°–25° C. for 1 hour and then at 60° C. for 18 hours under nitrogen. After removing most of the dimethylformamide at 50°–60° C. and 0.1 mm, the residue is partitioned between a 5% citric acid solution, 25 mL, and ethyl acetate, 75 mL. The ethyl acetate extract is washed with two 10 mL portions of water saturated with sodium chloride, dried over anhydrous sodium sulfate, filtered and concentrated at 40° C. and 15 mm. The residue is dried further at 20°–25° C. and 0.1 mm to give 6.5 g of the N-t-BOC derivative of methyldopa.

Step B. 4-Methyl-1,3-dioxol-2-one-5-ylmethyl(S)N-(t-Butoxycarbonyl)-3-hydroxy-α-methyltyrosinate A solution of N-(t-butoxycarbonyl)-3-hydroxy-α-methyltyrosine (760 mg, 2.44 mmol), triethylamine (263 mg, 2.60 mmol) and 4-bromomethyl-5-methyl-1,3-dioxol-2-one (500 mg, 2.60 mmol) in dimethylformamide, 10 mL, is stirred at 60° C. for 3 hours under nitrogen. Most of the dimethylformamide is removed at 50°–60° C. and 0.1 mm and the residue is partitioned between saturated sodium bicarbonate solution, 10 mL, and ethyl acetate, 50 mL. The ethyl acetate extract is washed with water saturated with sodium sulfate, filtered and concentrated at 40°–45° C. and 15 mm. Flash chromatography of the residue over 40 g of silica gel 60 (230–400 mesh) with 3% methanol-97% chloroform as eluent affords 320 mg of the desired ester.

Step C. 4-Methyl-1,3-dioxol-2-one-5-ylmethyl(S)3-Hydroxy-α-methyltyrosinate(2R,3R)hydrogentartrate hemihydrate A solution of 4-methyl-1,3-dioxol-2-one-5-ylmethyl(S)N-(t-butoxycarbonyl)-3-hydroxy-α-methyltyrosinate (1.24 g, 2.93 mmol) in ethyl acetate, 40 mL is cooled in an ice bath and saturated with anhydrous hydrogen chloride for 10 min. The solution is allowed to warm slowly to 20°–25° C. over 1.5 hours and then concentrated at 30°–40° C. and 15 mm. The residue is treated with a saturated sodium bicarbonate solution, 10 mL, and the deblocked ester is extracted into ethyl acetate, 50 mL. The ethyl acetate extract is washed with water saturated with sodium chloride, 10 mL, dried over anhydrous sodium sulfate, filtered and concentrated at 40°–45° C. and 15 mm. The ester base is converted to the (2R,3R) hydrogen tartrate hemihydrate salt, 370 mg, mp 123°–128° C. dec, with L-tartaric acid in a 95% ethanol-ethyl acetate solution.

Calc. for $C_{15}H_{17}NO_7 \cdot C_4H_6O_6 \cdot \frac{1}{2}H_2O$: C, 47.30; H, 5.01; N, 2.90. Found: C, 47.34; H, 5.05; N, 2.89.

The compound (4-t-butyl-1,3-dioxol-2-one-5-yl)methyl ester of methyldopa, as well as other 4-lower alkyl compounds, can be prepared in a similar fashion using analogous reactants. An example follows:

EXAMPLE 4

Preparation of 4-t-butyl-1,3-dioxol-2-one-5-ylmethyl(S)-3-hydroxy-α-methyl tyrosinate(2R,3R)hydrogentartrate hemihydrate Step A. 5-t-Butyl-4-methyl-1,3-dioxolen-2-one Forty-four g of a 12.5% solution of phosgene in toluene is added over 30 min to a well stirred solution of 4,4-dimethyl-2-hydroxy-3-pentanone (4.85 g, 37.3 mmol) in toluene, 90 ml, at 0°–5° C. Following this addition, a solution of pyridine, 11.4 ml, in toluene, 25 ml, is then added to the cooled reaction mixture over 30 min. After stirring at 20°–25° C. for 20 hours, the reaction mixture is washed with 3N HCl and water saturated with NaCl. The toluene extract is dried over anhydrous sodium sulfate, filtered and concentrated under reduced pressure. After addition of p-toluenesulfonic acid hydrate, 100 mg, to the residue, it is stirred neat at 160° C. for 24 hours. The resulting black liquid is dissolved in ethyl acetate, washed with a saturated sodium bicarbonate solution and a saturated sodium chloride solution and dried over anhydrous sodium sulfate. After filtering and concentrating under reduced pressure, the residue is distilled to give 3.5 g of product, bp 82°–4° C. at 3 mm.

Step B. 4-Bromomethyl-5-t-butyl-1,3-dioxolen-2-one

A mixture of 4-methyl-5-t-butyl-1,3-dioxolen-2-one (3.5 g, 22.4 mmol), N-bromosuccinimide (4.16 g, 23.4 mmol) and dibenzoylperoxide (20 mg) in carbon tetrachloride (100 ml) is stirred at reflux for one hour. After filtering, the filtrate is concentrated under reduced pressure to give the 4-bromomethyl derivative as an oil.

Step C. 4-t-Butyl-1,3-dioxol-2-one-5-ylmethyl(S)3-hydroxy-α-methyltyrosinate(2R,3R)hydrogentartrate hemihydrate A mixture of 4-bromomethyl-5-t-butyl-1,3-dioxolen-2-one (5.27 g, 22.4 mmol) and (S)3-hydroxy-α-methyltyrosine sesquihydrate (5.3 g, 22.4 mmol) in dry dimethylformamide (35 ml) is stirred at 20°–25° C. for three hours under nitrogen. Solvent is removed at 40°–50° C. and 0.1–0.3 mm pressure and the residue is partitioned between a saturated aqueous sodium bicarbonate solution and ethyl acetate. The ethyl acetate extract is washed with water saturated with sodium chloride, dried over anhydrous sodium sulfate, filtered and concentrated. The crude ester is converted to the (2R,3R) hydrogen tartrate salt and recrystallized from an 95% ethanol-ethyl acetatehexane mixture to give 6.75 g (57.4%) of the desired ester as the hydrogentartrate hemihydrate salt, mp=113°–121° C., slow decomposition.

Anal. Calcd. for $C_{18}H_{23}NO_7 \cdot C_4H_6O_6 \cdot \frac{1}{2}H_2O$: C, 50.38, H, 5.77, N, 2.67. Found: C, 50.40, H, 5.85; N, 2.54.

What is claimed is:

1. The (5-alkyl-2-oxo-1,3-dioxolen-4-yl)methyl ester of a carboxylic acid wherein alkyl has 1–6 carbon atoms and wherein said carboxylic acid is cefoxitin, methyldopa, 3β-[2-methoxyimino-2-(2-amino-1,3-thiazolol-4-yl)acetamido]monobactamic acid, 2-ethylthio)-6β-(1R-hydroxyethyl)-penem-3-carboxylic acid or fosfomycin.

2. The compound of claim 1 wherein the carboxylic acid is cefoxitin.

3. The compound of claim 1 wherein the carboxylic acid is methyldopa.

4. The compound of claim 1 wherein the carboxylic acid is 3β-[2-methoxyimino-2-(2-amino-1,3-thiazol-4-yl)acetamido]monobactamic acid.

5. The compound of claim 1 wherein the carboxylic acid is 2-(ethylthio)-6β-(1R-hydroxyethyl)penem-3-carboxylic acid.

6. The compound of claim 1 wherein the carboxylic acid is fosfomycin.

7. The compound 4-t-butyl-1,3-dioxol-2-one-5-ylmethyl(S)-3-hydroxy-α-methyltyrosinate(2R,3R)hydrogentartrate, and in hemihydrate form.

8. The compound 4-methyl-1,3-dioxol-2-one-5-ylmethyl(S)-3-hydroxy-α-methyltyrosinate(2R,3R)hydrogentartrate, and in hemihydrate form.

9. A pharmaceutical composition containing an effective amount of the compound of any one of claims 1 through 8 in a pharmaceutically acceptable carrier.

10. The compound of claim 1 wherein said alkyl is other than methyl.

11. The compound of claim 1 wherein said alkyl is t-butyl.

* * * * *